United States Patent
Nilsson et al.

(10) Patent No.: US 9,011,382 B2
(45) Date of Patent: Apr. 21, 2015

(54) VASCULAR ACCESS DEVICE BLOOD SEALING AND EXPOSURE PREVENTION

(75) Inventors: Bengt Erik Anders Nilsson, Helsingborg (SE); Janne Joakim Lundqvist, Vellinge (SE); Kristoffer Glowacki, Staffanstorp (SE); Karl Johan Mårten Söderholm, Helsingborg (SE); Lars-Åke Lennart Larsson, Lund (SE); Johan Fredrik Thörne, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 584 days.

(21) Appl. No.: 11/943,352

(22) Filed: Nov. 20, 2007

(65) Prior Publication Data
US 2008/0147009 A1 Jun. 19, 2008

Related U.S. Application Data

(60) Provisional application No. 60/867,050, filed on Nov. 22, 2006.

(51) Int. Cl.
*A61M 5/178* (2006.01)
*A61M 25/06* (2006.01)
*A61M 5/32* (2006.01)

(52) U.S. Cl.
CPC ....... *A61M 25/0637* (2013.01); *A61M 25/0606* (2013.01); *A61M 25/0625* (2013.01); *A61M 5/3275* (2013.01); *A61M 2005/3247* (2013.01)

(58) Field of Classification Search
USPC ............... 604/158, 162, 164.01, 164.02, 604/167.01–167.04, 167.06, 168.01
See application file for complete search history.

(56) References Cited

U.S. PATENT DOCUMENTS

| | | | |
|---|---|---|---|
| 3,802,433 A | 4/1974 | Raven | |
| 4,133,304 A * | 1/1979 | Bailey | 600/577 |
| 4,231,367 A | 11/1980 | Rash | |
| 4,666,438 A * | 5/1987 | Raulerson | 604/272 |
| 5,030,205 A | 7/1991 | Holdaway et al. | |
| 5,053,017 A | 10/1991 | Chamuel | |
| 5,092,845 A | 3/1992 | Chang | |
| 5,156,792 A | 10/1992 | Holdaway et al. | |

(Continued)

FOREIGN PATENT DOCUMENTS

| | | |
|---|---|---|
| EP | 1595568 | 11/2005 |
| GB | 2277032 | 10/1994 |

(Continued)

*Primary Examiner* — Nicholas Lucchesi
*Assistant Examiner* — Gerald Landry, II
(74) *Attorney, Agent, or Firm* — Jeanne Lukasavage; Craig Metcalf; Kirton McConkie

(57) ABSTRACT

An extravascular system for accessing the vasculature of a patient including a catheter having an interior surface, a needle disposed within the catheter, and/or a needle cap defining at least one capillary space and including a flexible seal surrounding the at least one capillary space. The flexible seal may engage the interior surface of the catheter. A method of controlling exposure to a liquid from an extravascular system including providing a wicking material positioned adjacent to a flow channel such that any fluid located external to the flow channel is retained by the wicking material. The wicking material may be incorporated into any extravascular system where exposure to liquids is undesirable.

20 Claims, 6 Drawing Sheets

(56) References Cited

U.S. PATENT DOCUMENTS

| | | | | |
|---|---|---|---|---|
| 5,201,712 A | * | 4/1993 | Bryant | 604/164.02 |
| 5,447,501 A | * | 9/1995 | Karlsson et al. | 604/198 |
| 6,527,747 B2 | | 3/2003 | Adams et al. | |
| 2001/0007641 A1 | * | 7/2001 | Jovanovich et al. | 422/99 |
| 2004/0017981 A1 | * | 1/2004 | Jovanovich et al. | 385/68 |
| 2007/0270635 A1 | * | 11/2007 | Schellenberg | 600/101 |

FOREIGN PATENT DOCUMENTS

| | | |
|---|---|---|
| JP | 2002-58746 A1 | 2/2002 |
| JP | 2006-297062 A | 11/2006 |
| WO | WO9308865 | 5/1993 |
| WO | WO9528979 | 11/1995 |
| WO | WO2005004959 | 1/2005 |
| WO | WO2005087296 | 9/2005 |

\* cited by examiner

VASCULAR ACCESS DEVICE BLOOD SEALING AND EXPOSURE PREVENTION

RELATED APPLICATIONS

This application claims the benefit of U.S. Provisional Application No. 60/867,050, filed Nov. 22, 2006, entitled VASCULAR ACCESS DEVICE BLOOD SEALING AND EXPOSURE PREVENTION, which is incorporated herein by reference.

BACKGROUND OF THE INVENTION

This invention relates generally to vascular access devices and methods, including catheter assemblies and devices used with catheter assemblies. Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally looks for confirmation of the access. This confirmation may be dependent on good venting of the catheter adapter. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter. This is not always possible due to different reasons like: no time available, difficult vein, or lack of experience. In some other situations the clinician may need additional vein access confirmation in the catheter adapter and for that reason allows blood flow into the adapter.

The clinician may then withdraw the introducer needle from the catheter. The introducer needle may be withdrawn into a needle tip shield or needle cap that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to prevent clinicians from unanticipated blood exposure from needle sticks and other exposure from blood collected on or in the needle tip.

In devices where blood travels to the needle tip shield, an operator of the needle tip shield may be exposed to the blood when the needle tip shield is removed from the catheter adapter. Thus, various systems and methods are needed to provide needle tip shields that interface with other vascular access devices such as catheters, minimize exposure to and contamination by blood contained in, on, or around the needle tip shield, and/or provide blood flashback at least to the point of the needle tip shield within the catheter adapter.

BRIEF SUMMARY OF THE INVENTION

The present invention has been developed in response to problems and needs in the art that have not yet been fully resolved by currently available extravascular systems and methods. Thus, these systems and methods are developed to provide more efficient extravascular systems and methods capable of minimizing exposure to and contamination by blood contained in, on, or around needle tip shields, and/or providing blood flashback at least to the point of a needle tip shield within a catheter adapter.

An extravascular system for accessing the vasculature of a patient may include a catheter having an interior surface, a needle disposed within the catheter, and/or a needle cap defining at least one capillary space and including a flexible seal surrounding the at least one capillary space. The flexible seal may engage the interior surface of the catheter adapter. The extravascular system may also include a needle hub, a foil securing the needle cap to the needle hub, a flow control plug secured to the needle hub, and/or a vent plug secured to the flow control plug.

The needle may include a needle tip, and the needle may define a notch between the needle and the catheter. Blood may flow along the entire length of the extravascular system from the needle notch to the clip house of the needle cap where the mechanism for shielding the needle tip is housed. The controlled air/blood flow through the product, especially the controlled air/blood flow through needle cap vent, the vent being defined as the space between the needle and the hole of the needle cap through which the needle extends, may define a controlled blood flow (sometimes referred to as "flashback") chamber. The extravascular system may define a blood flow space along the entire length of the extravascular system, and the blood flow space may be formed to provide controlled blood flow during operation of the system.

The at least one capillary space, which may be of any geometry capable of creating capillary forces, may receive and retain blood when the needle cap is removed from the catheter. The needle cap may define a port through which the needle may extend, and the system may also include at least three, and/or at least six, capillary spaces spaced equally around the port through which the needle may extend. The capillary spaces may be spaced equally in revolver formation around the hole through which the needle may extend.

The flexible seal may include a tube having a sealing surface on the exterior surface of the tube. The flexible seal may include at least one pleat formed within the interior surface of the tube. The flexible seal may include a pleated skirt, a prolonged tube, a slit skirt, an elastomeric O-ring, and/or a septum. The septum may be formed within the interior surface of the catheter adapter and may surround a portion of the needle cap when the needle cap is engaged with the catheter adapter.

A method of manufacturing an extravascular system may include providing a catheter adapter having an interior surface, disposing a needle within the catheter adapter, providing a needle cap, forming at least one capillary space within the needle cap, forming a flexible seal surrounding the at least one capillary space, and/or engaging the interior surface of the catheter with the flexible seal. The method may also include providing a needle hub, providing a tether, securing the needle cap to the needle hub with the foil, providing a needle port through the needle cap, inserting a needle through the needle port thereby providing a needle cap vent between the needle and the needle port.

The needle may include a needle tip, and the method may also include forming a notch in the needle between the needle and the catheter, and forming a path through the extravascular system through which fluid may flow. The method may also include controlling the flow of fluid through a path and/or forming a flashback chamber within the needle cap vent. The method may also include forming at least one capillary space to receive and retain blood when the needle cap is removed from the catheter, forming at least three capillary spaces spaced equally around the port through which the needle may extend, and/or forming at least six capillary spaces spaced equally in revolver formation around the port through which the needle may extend. While this describes one embodiment, any combination of geometries capable of generating capillary forces should be considered within the scope of the present invention.

Forming a flexible seal may include forming a tube having a sealing surface on the exterior surface of the tube; forming at least one pleat within the interior surface of the tube; and/or forming at least one of a pleated skirt, a slit skirt, a prolonged tube, an elastomeric O-ring and/or a septum or other flexible material.

An extravascular system for accessing the vasculature of a patient may include a catheter adapter, a needle, and a needle cap. The catheter adapter may have an interior surface. The needle may be disposed within the catheter adapter. The needle cap may define at least one means for retaining blood within the needle cap. The needle cap may include at least one means for sealing the at least one means for retaining blood within the needle cap. The means for sealing may communicate with the interior surface of the catheter adapter.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL
VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1 includes a perspective view of an extravascular system in a pre-use configuration.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
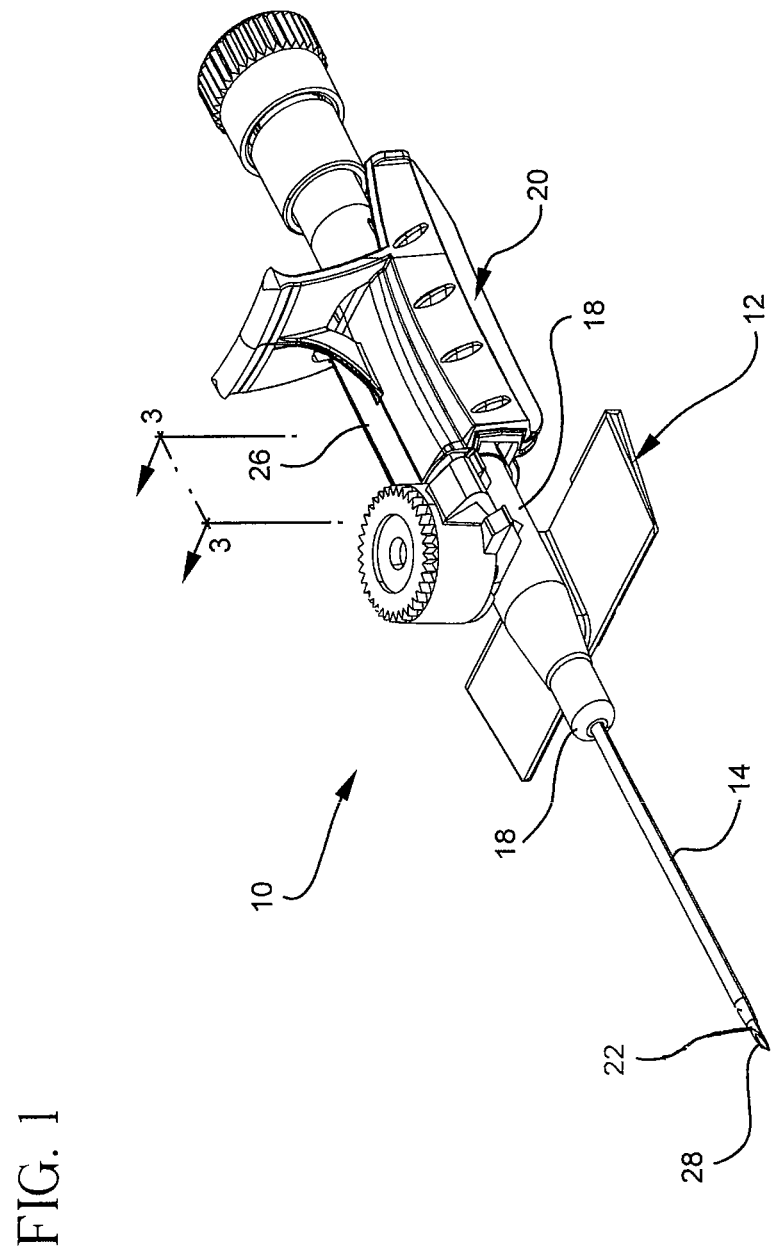

Referring to FIG. 1, a perspective view illustrates an example of an extravascular system 10 prior to insertion. In this example the extravascular system 10 includes a catheter assembly 12, which is shown in its entirety. The catheter assembly 12 includes multiple component parts that will be described in greater detail in connection with FIG. 2.

Figure 2:
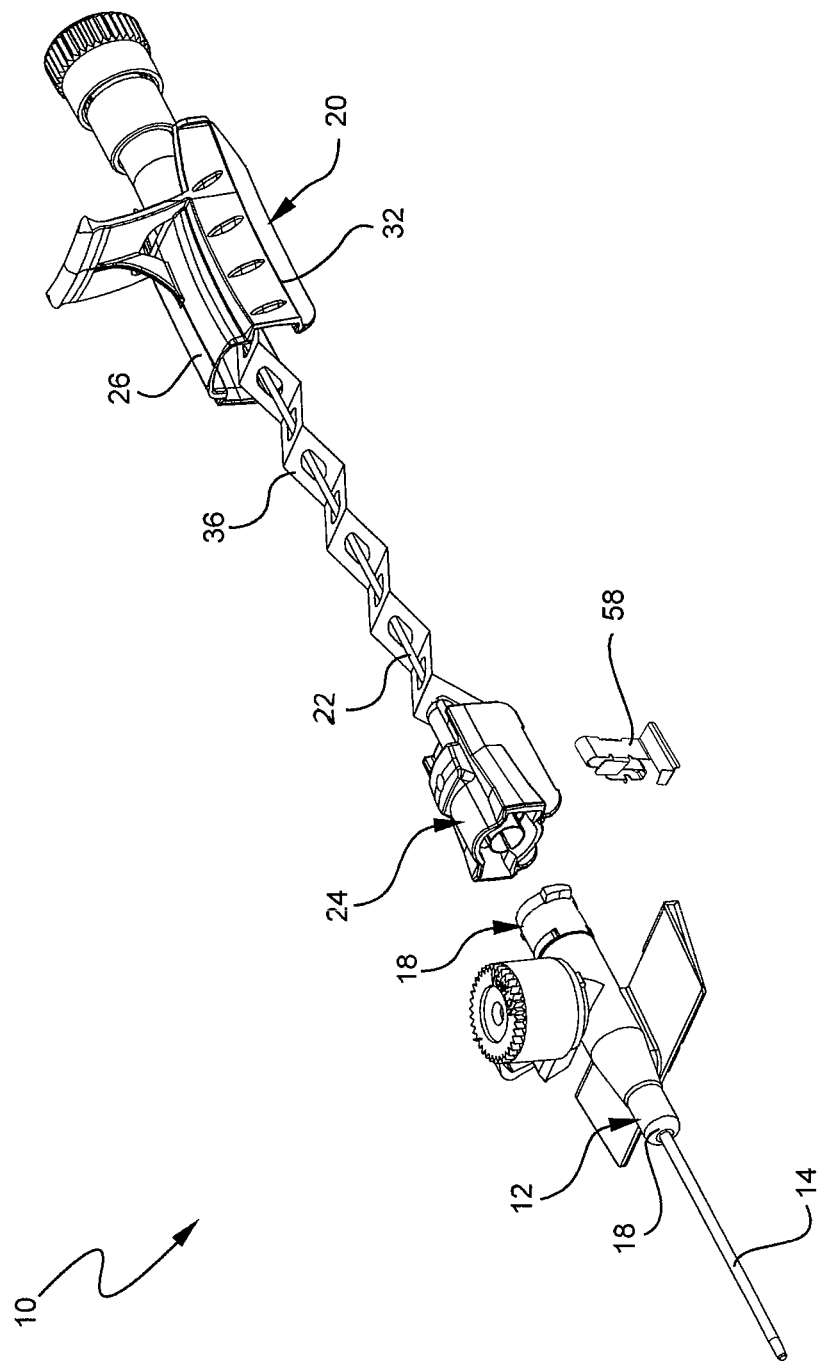
FIG. 2 is a perspective view of the extravascular system of FIG. 1 having the needle cap deployed including an exploded view of the clip housing.

Referring now to FIG. 2, a perspective view illustrates a deployed needle assembly 20 after it has been separated from other components of the catheter adapter 18. The catheter assembly 12 includes cooperating elements such as a catheter adapter 18 and a catheter 14. The catheter adapter 18 may be configured to cooperate with the needle assembly 20 during insertion of the catheter 14 and to provide other functions after the needle assembly 20 is removed.

The exploded view of FIG. 2 further illustrates that the extravascular system 10 includes a needle assembly 20. The needle assembly 20 may include a variety of subcomponents, some examples of which are shown in FIG. 2. The needle assembly 20 may include a needle 22 adapted to be inserted into the vascular system of a patient and to facilitate the insertion of the catheter 14 to the vascular system of a patient. Additionally, the needle assembly 20 may include a needle cap 24, a needle hub 26, and a tether 28 extending between the needle cap 24 and the needle hub 26. As can be seen by comparing FIGS. 1 and 2, the needle cap 24 and the tether 28 may be adapted to fit at least substantially inside the needle hub 26 when the needle assembly 20 is in the pre-use configuration. The needle assembly 20 may include additional parts or components adapted to provide the needle assembly 20 with the desired functionality. Similarly, the catheter adapter 18 may include additional or alternative parts and subcomponents depending on the configuration of the extravascular system 10 and its intended usage.

For example, the needle hub 26 may be provided in a variety of configurations depending on the intended usage of the extravascular system 10 in which the needle assembly 20 is used. In one embodiment, the needle hub 26 may include features to improve the user's grip on the needle hub 26, to improve the user's ability to maneuver the needle assembly 20, and/or to provide other functionality to the needle hub 26 and/or the needle assembly 20 generally. In another embodiment, the needle cap 24 and the needle hub 26 may be adapted to allow at least a substantial portion of the needle cap 24 to be disposed within the needle hub 26 prior to deployment of the needle cap 24. Additionally, the needle cap 24 may be provided with elements adapted to selectively couple the needle cap 24 to the catheter adapter 18 such that when the needle assembly 20 is withdrawn from the catheter adapter 18 the needle cap 24 is separated from the needle hub 26 and drawn into the deployed position of FIG. 2. Additionally, the needle cap 24 may include lock-out mechanisms that control or limit the movement of the needle cap 24 relative to the needle 22 once the needle cap 24 is disposed in the deployed condition.

In some uses of the extravascular system 10, some amount of the patient's blood may persist on the needle assembly 20, and particularly on the distal tip of the needle 22, after the needle assembly 20 is separated from the catheter adapter 18.

In some configurations of the needle cap 24, the needle cap 24 may include shields, reservoirs, caps, or other features adapted to minimize the possibility of spilling this blood and/or the possibility of users unintentionally contacting this blood. As evidenced by this list of variations and features that may be incorporated into the needle cap 24, numerous configurations of the needle cap 24 are within the scope of the present disclosure, some of which may include one or more of the features described herein.

For example, the preferred embodiment of the present invention comprises a needle cap 24 including a shield 58 and a shield housing cover. The shield 58 may be a V-shaped metal clip or similar mechanical structure provided to prevent the needle 22 from reemerging beyond the needle cap 24 after the needle assembly 20 is separated from the catheter adapter 18. The shield housing cover encloses the shield 58 thereby providing containment of any fluids that may enter the needle cap 24 during insertion of the catheter 13 into a patient, and following removal of the needle assembly 20 from the catheter adapter 18. The needle cap 24 of the present invention is further modified to include a front vent, a needle entry vent and a system of capillaries, discussed in detail below (see FIGS. 3-5).

Still referring to FIG. 2, the tether 28 of the needle assembly 20 is illustrated in its deployed condition coupling the needle cap 24 to the needle hub 26. The tether 36 is illustrated as being initially folded within the needle hub 26 and then unfolded and stretched along the needle 22 as the needle cap 24 and tether 36 are deployed. While the tether 28 may include holes through each panel of the folded tether 36 to form a needle passage, such a passage is not required. For example, the tether 36 may be adapted to be folded, or otherwise compacted, within the needle hub 26 without requiring passage of the needle 22. Additionally or alternatively, other suitable relationships between the needle 22 and the tether 36 may be implemented. The tether 36 may be made of conventional materials to provide the desired strength, sterility, and other properties. The tether 36 may be adapted to have a maximum deployed length that is selected to prevent the needle cap 24 from being separated from the needle assembly 20, such as being pulled from the distal end of the needle 22.

In an extravascular system 10 where controlled blood flow, or flashback, extends into, on, and/or around the needle cap 24, when the needle tip 44 is withdrawn into the needle cap 24, and the needle cap 24 is disengaged from the catheter adapter 18, a user may be exposed to blood from the needle cap 24. Thus, features and elements within, on, and/or around the needle cap 24 are desired in order to avoid blood from spilling from the needle cap 24 as the needle cap 24 is removed from the catheter adapter 18.

Figure 3:
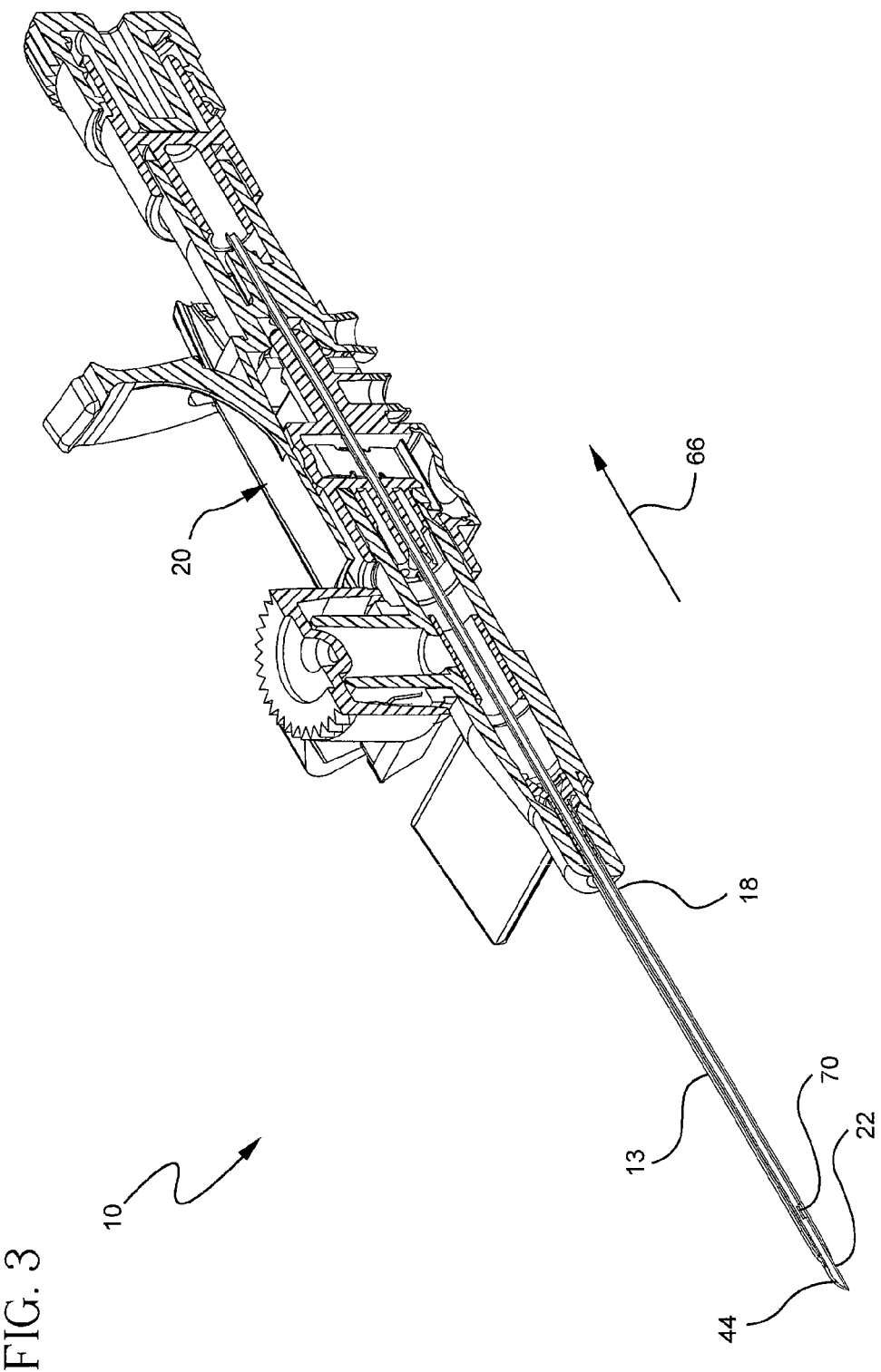
FIG. 3 is a cutaway view of the extravascular system of FIG. 1 in a pre-use configuration.
Figure 3A:
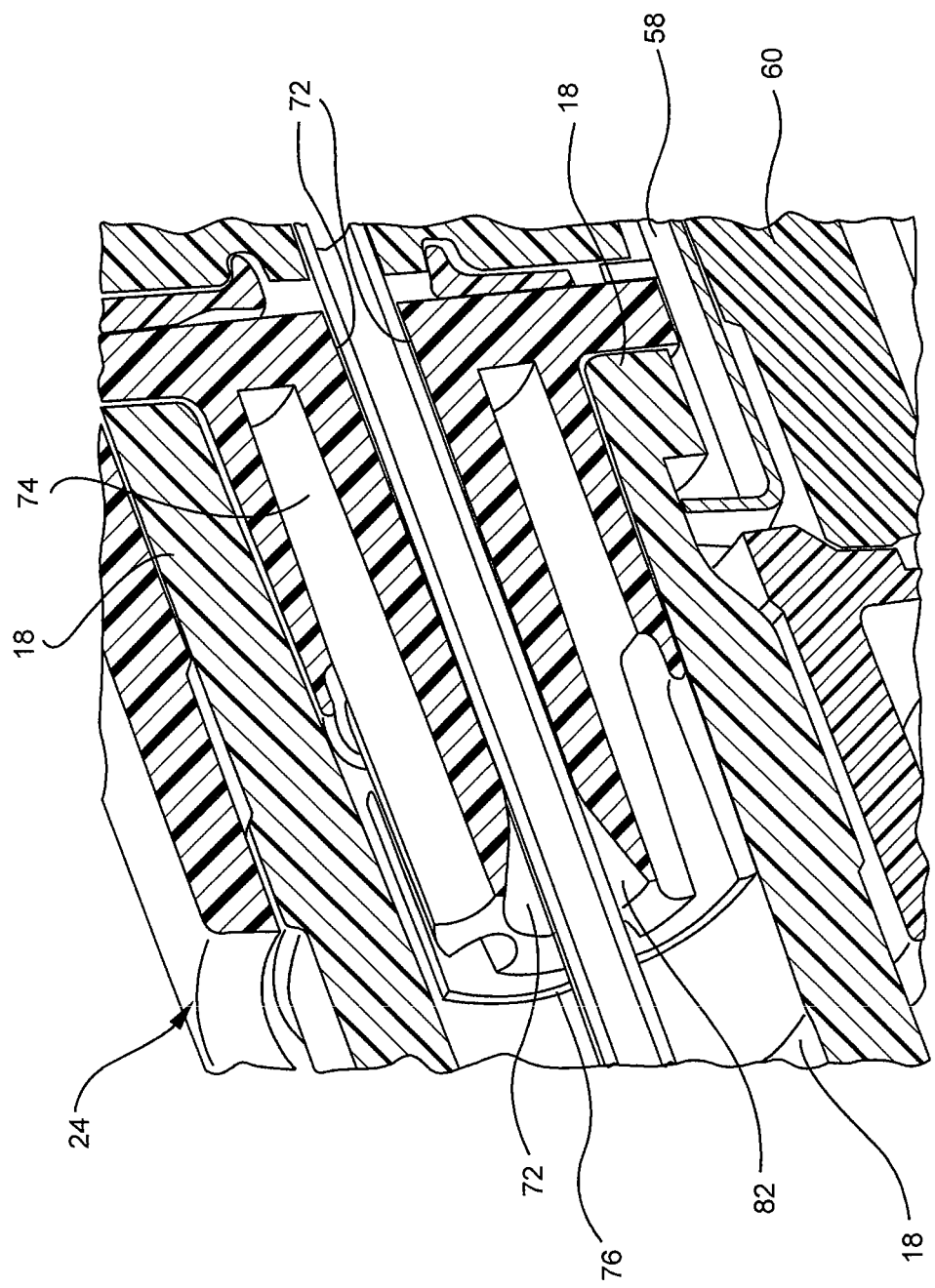
FIG. 3a is a partial cross section view of an extravascular device detailing the interface between the catheter adapter, the needle and the needle clip.

Referring to FIGS. 3 and 3a, a cross section view of the extravascular system 10 illustrating the needle 22, the catheter 13, the needle cap 24, and the needle assembly 20 is shown. The cross section reveals the direction of flow 66 for the blood and air within a section of the extravascular system 10. In certain extravascular systems 10, blood enters the needle tip 44 and into the lumen of the needle 22. In order to provide controlled blood flow (flashback) in such catheter assemblies, a notch 70 is formed within the side of the needle 22 where the needle 22 is enclosed at the notch 70 by another structure within the extravascular system 10, such as the catheter 13. The notch 70 provides a means whereby some blood may escape the inner lumen of the needle 22 and travel between the outer diameter of the needle 22 and the inner diameter of the other device, such as the catheter 13. An operator may then visualize the flow of blood through the catheter 13 and/or any other translucent material of any device within the extravascular system 10.

As discussed earlier, the needle cap 24 is eventually removed from the catheter adapter 18, providing an opportunity for the blood in, on, and/or around the needle cap 24 to spill and potentially contaminate and/or harm an operator of the extravascular system 10. The portion of the needle cap 24 comprising the needle cap front vent 72, the front vent 72 being the space through which blood travels through the needle cap 24, must therefore be modified and/or controlled in order to prevent blood from spilling from the needle cap 24 after its disengagement from the catheter adapter 18. Capillary tubes 74 may be formed within this portion of the needle cap 24 in order to retain, via surface tension, the blood that comes into contact with the needle cap 24 after the needle cap 24 is disengaged from the catheter adapter 18.

Referring to FIG. 3a, a close-up view of the capillary tubes 74 of the needle cap 24 as secured to the catheter adapter 18 within the extravascular system 10 is shown. The capillary tubes 74 are surrounded by a seal surface 76 which comes into contact with the catheter adapter 18 in order to ensure that blood does not leak between the seal surface 76 and the catheter adapter 18. Thus, blood will travel from the interior of the catheter adapter 18 and into the capillary tubes 74 and the front vent 72 between the needle 22 and the interior surface of the needle port 82 within the needle cap 24. As blood travels through the catheter adapter 18 and into the needle cap 24, the process of capillary action will draw blood into the capillary tubes 74.

The capillary tubes 74 may include any material and/or configuration of material beneficial in preventing unintended exposure to blood or other liquids where unintended exposure is undesirable. For example, as illustrated the capillary tubes 74 comprise tubes molded within the material of the needle cap 24. However, in another embodiment the capillary tubes 74 comprise a configuration of fibrous materials having wicking properties wherein the fibrous materials are positioned such that upon separation of the needle cap 24 from the catheter assembly 18 the fibrous materials absorb and/or retain any residual liquids not contained within the needle cap 24 and/or the catheter adapter 18. Additional embodiments contemplate the use of other capillary-like materials that may absorb and/or retain fluids thereby preventing unintended exposure to the liquid.

Figure 4:
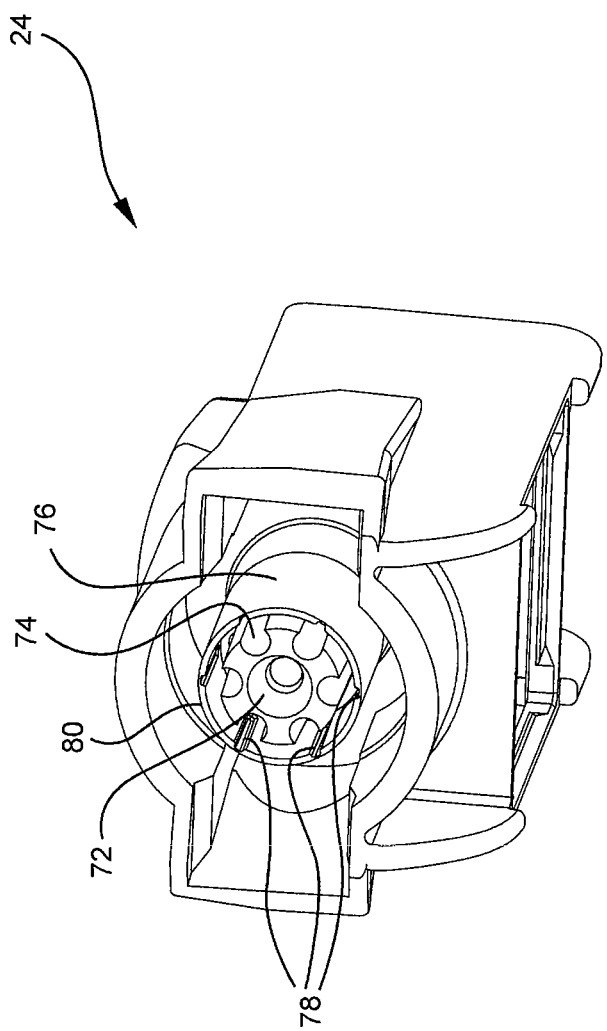
FIG. 4 is a perspective view of a needle cap.

Referring to FIG. 4, a perspective view of the needle cap 24 is shown. The needle cap 24 includes six revolver holes, or capillary tubes 74, surrounding the front vent 72 through which blood will travel through the needle cap 24 and into the clip housing 50. The capillary tubes 74 are in turn each surrounded by a tube 80 having a sealing surface 76. The tube 80 having the sealing surface 76 forms the interface with a catheter adapter 18. The sealing surface 76 may be a smooth surface to which the interior surface of the catheter adapter 18 may seal in order to ensure that no air or blood travels in between the interior surface of the catheter adapter 18 and the sealing surface 76.

In order to ensure a fit with the lowest possible separation force between the sealing surface 76 and the interior surface of the catheter adapter 18, various pleats 78 within the surface of the tube 80 that is opposite the sealing surface 76 may be formed. The pleats 78 are a lack of material within the surface opposite the sealing surface 76 in the tube 80 in order to enable the tube 80 to buckle and/or compress towards the front vent 72 as the inner surface of the catheter adapter 18 exerts pressure upon the sealing surface 76. After the pleats 78 are compressed and the inner surface of the catheter adapter 18 is sealed against the sealing surface 76, the natural force of the tube 80 will bias itself to open the pleats 78.

Figure 5:
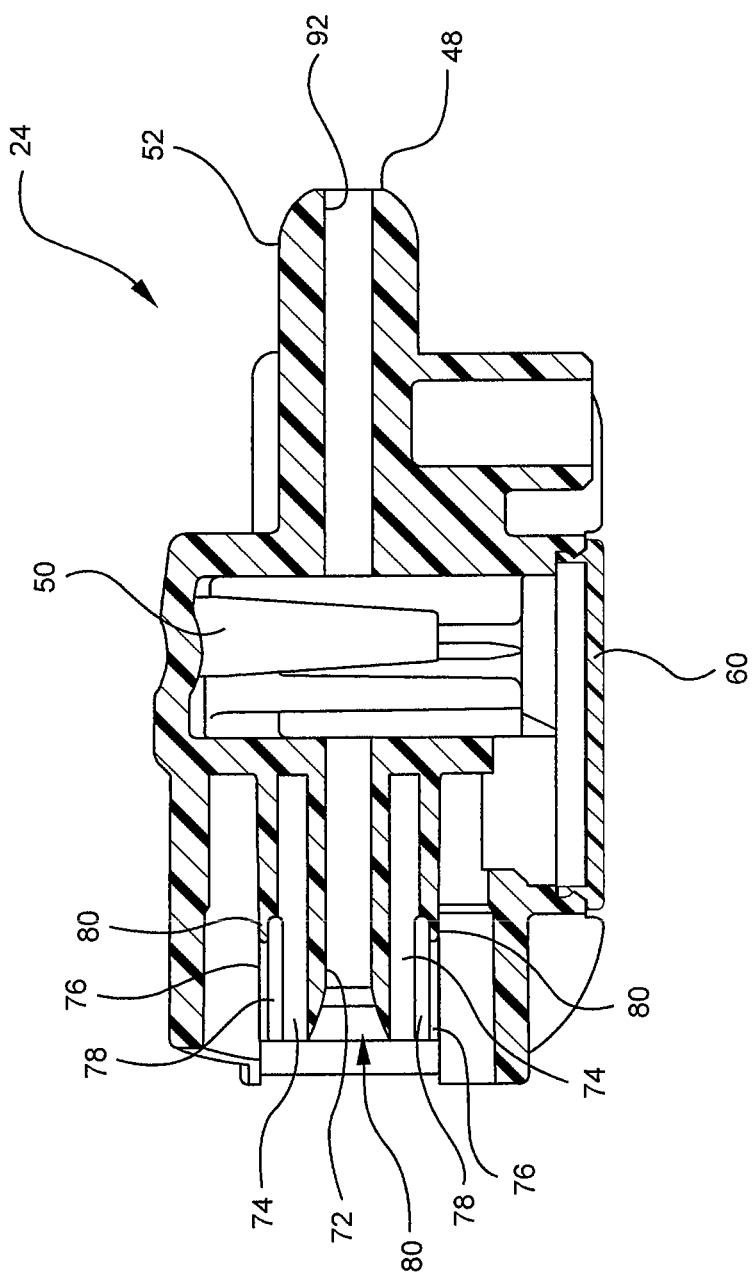
FIG. 5 is a cross section of the needle cap.

FIG. 5 illustrates the needle cap 24 and its components. The needle cap 24 displayed in FIG. 5 includes some or all of the features described herein.

FIG. 5 illustrates a cut away side view of the needle cap 24 comprising a nose or feature including a tube 80 having multiple capillary tubes 74 and a front vent 72. The needle cap 24 includes a cylindrical sealing surface 76 which seals against the inner surface of the catheter adapter 18 and forces all air and blood to flow between the needle cap 24 and the outer diameter of the needle 22 within the front vent 72. The small cavities, revolver holes, and/or capillary tubes 74 within the needle cap 24 retain, by capillary action, any blood which may contaminate the needle cap 24 during needle 22 removal from the catheter adapter 18. By providing blood retention, the needle cap 24 solves the problems inherent with previous devices which suffer from uncontrolled blood exposure when such devices were removed from catheter adapters or similar extravascular systems.

The needle cap 24 further comprises a rear extension 52 wherein the needle entry port 48 is located. The needle entry port 48 provides a path through the rear extension 52 of the needle cap 24, though which the needle 22 may extend. The rear vent 92 defining the space between the needle 22 and the needle entry port 48 provides a flow path for air and/or blood exiting the clip housing 50 during insertion of the catheter 13 into a patient and/or during removal of the needle cap 24 from the catheter adapter 18.

Referring now generally to FIGS. 1 through 5, the needle cap 24 provides additional benefits to an extravascular system 10 than those discussed above. For example, because the needle cap 24 limits blood spilling and/or exposure as a result of the capillary tubes 74, the extravascular system 10 may provide flashback of blood up to and beyond the needle cap 24. In the embodiments discussed above, providing a sealed engagement between the tube 80 of the needle cap 24 and the catheter adapter 18 as well as providing a pair of vents 72 and 92 enables air and/or blood to flow through the entire extravascular system 10. By enabling air and blood to travel beyond the needle cap 24, the vacuum that would otherwise exist between the needle cap 24 and the catheter adapter 12 does not exist, and suction exerted upon the interior lumen of the catheter adapter 18 is limited as the needle cap 24 is removed from the catheter adapter 18. The lack of suction avoids a problem that occurs in other devices that can be described as a pump effect which results in blood being suctioned from the catheter adapter 18 as the needle cap 24 is removed from the catheter adapter 18. This pump or suction effect in other devices causes additional blood spillage and contamination during removal of the needle cap.

The needle cap 24 design as described above also includes additional benefits over previous devices. For example, the tube 80 including the sealing surface 76 and the pleats 78 requires less insertion and removal force into and out of the catheter adapter 18. Because the tube 80 is able to seal with minimal insertion force against the inner surface of the catheter adapter 18, little to no blood and/or air escapes the catheter adapter 18 through the seal between the inner surface of the catheter adapter 18 and the sealing surface 76 of the tube 80. Further, because the tube 80 includes pleats 78 on the surface opposite the sealing surface 76, the needle cap 24 may be removed with minimal force from the adjoining inner surface of the catheter adapter 18. Removing the needle cap 24 with minimal force from the catheter adapter 18 will provide a smoother, less abrupt separation of the needle cap 24 from the catheter adapter 18 that would otherwise cause additional blood spillage and exposure.

Further, separating the needle cap 24 from the catheter adapter 18 may require two hands where the separation force is too great. Since a clinician or operator of the extravascular system 10 may need their other hand to occlude the vasculature of a patient during removal of the needle cap 24 from the catheter adapter 18, a lower separation force as provided by the system described herein is advantageous. The lower separation force is enabled by providing a flexible sealing surface using pleats 78 and/or any other feature capable of providing a flexible sealing surface not previously provided by traditional needle caps.

A lower separation force provided by the systems described herein enables an operator or clinician to occlude the vasculature of the patient while the needle cap 24 is removed from the catheter adapter 18, thus minimizing or eliminating any blood that would otherwise flow from the catheter adapter 18 into, on, and/or around the needle cap 24. Any blood that does escape from the catheter adapter 18 into, on, and/or around the needle cap 24 will be absorbed by the capillary tubes 74 of the needle cap 24 and retained by the capillary tubes 74 as a result of the surface tension of the blood in connection with the capillary tubes 74. The capillary tubes 24 thus provide a structure capable of permanently maintaining blood within the needle cap 24 after its separation from the catheter adapter 18 and through to its final disposal within a safety container.

The front and rear vents 72 and 92 are preferably formed to provide a flow of blood at a controlled rate through the preferably translucent material of the needle cap 24 in order to provide information to an operator or clinician regarding whether the needle tip 44 and/or the catheter 13 was and remains properly located within the vasculature of the patient during operation of the catheter assembly 12. This allow clinicians to see blood in the catheter adapter providing information to the operator or clinician as to how strong the blood flow is within the vein. A strong blood flow rate is also indicative of proper location of the needle tip 44 and/or catheter 13.

The tube or pleated skirt 80 may be designed as an integral part of the needle cap 24 and may consist of a thin, flexible pleated cylinder creating a seal by a press fit onto the catheter adapter 18. The thin and pleated structure 80 ensures that only a small force is generated from the skirt onto the catheter adapter 18, which in turn ensures, as discussed above, that a low force is required to separate the catheter adapter 18 from the needle cap 24. This seal and low separation force results in a very robust seal function that is not dependent on any molding process variations. The successful seal then forces air and blood to flow through the remainder of the catheter adapter 18 and the attached needle cap 24 providing an operator or clinician with more time for insertion and fixation of the catheter 13, or other operation of the vascular access devices of the catheter adapter 18. The controlled volume of the front and rear vents 72 and 92, as mentioned previously may be tuned to optimize air/blood flow and air/blood flow rate through the catheter adapter 18 and the attached needle cap 24.

For example, the blood flow rate through the extravascular system 10 may be increased by increasing the bore of the front vent 72 such that the space between the needle 22 and the needle port 82 is increased thereby increasing the volume of the front vent 72. Additionally, the bore of the rear vent 92 may be increased thereby providing greater venting to the clip housing 50 causing decreased backpressure within the extravascular system 10 and allowing increased blood/air flow therein. To establish a good balance between leakage and venting there has been developed an optimal relation between the size of the front vent 72 and its length versus the needle size (outside diameter). This relation will enable good performance for vein indication (flashback) but still prevent blood leakage within a normal insertion time.

Any number of alternative embodiments may replace the pleated skirt or tube 80 in order to provide a press fit seal between the catheter 12 and the needle cap 45. For example, a solid cone may be docked into the catheter adapter 18. A slit skirt having various depths and lengths and numbers of pleats may be employed. An elastomeric ring on the needle cap tube 80 such as an O-ring may be employed. Sealing between the catheter adapter 18 and the needle cap 24 may be provided by an elongated tube 80. Further, a septum may be provided within the inner volume of the catheter adapter 18.

The capillary tubes 74 need not be arranged in a revolver type orientation where each capillary tube surrounds the front vent 72 within the needle cap 24. Any number, size, and/or location of capillary tubes 74 or other capillary spaces may be provided in order to receive blood through capillary action and retain blood through surface tension. The embodiment of capillary tubes 74 arranged in a revolver orientation may be preferable in order to ensure a uniform capture, distribution, and retention of blood within the needle cap 24. Such uniform retention may be preferable, since during removal and handling of the needle cap 24, force that would cause blood to spill from the needle cap 24 may be exerted in any direction. The revolver orientation of the capillary tubes 74 is a multi-directional orientation. The various elements and features of the capillary tubes may be adjusted in order to achieve an optimal retention of blood to prevent splash up to a maximum acceleration. For example, as previously discussed the capillary tubes 74 may comprise any material and/or combination of materials with wicking and/or adsorbing properties that would be beneficial in preventing undesirable exposure to liquids during use of the extravascular system 10.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
a catheter adapter having a proximal end and a distal end;
a catheter that extends from the distal end of the catheter adapter; and
a needle assembly, the needle assembly comprising:
a needle hub configured to attach to the proximal end of the catheter adapter;
a needle having a proximal end secured within the needle hub and a distal end that extends out through the distal end of the catheter when the needle hub is attached to the catheter adapter; and
a needle cap having a needle port forming an opening through the needle cap, wherein the needle cap is contained within the needle hub when the needle hub is attached to the catheter adapter such that the distal end of the needle extends out through the needle port, whereas, when the needle hub is removed from the catheter adapter, the needle cap extends to a position overtop the distal end of the needle thereby securing the distal end of the needle within the needle cap, the needle cap including a plurality of capillary tubes that extend in parallel with at least a portion of the needle port, each capillary tube having a distal opening that is positioned adjacent to a distal opening of the needle port such that blood that exits the distal end of the needle port is collected within the capillary tubes to thereby prevent the blood from exiting the needle cap.

2. The catheter assembly of claim 1, wherein the needle assembly further comprises a tether that secures the needle cap to the needle hub when the needle hub is removed from the catheter adapter.

3. The catheter assembly of claim 1, wherein the needle cap includes a shield that prevents the distal end of the needle from reemerging from the needle cap once the distal end of the needle is secured within the needle cap.

4. The catheter assembly of claim 1, wherein the needle cap comprises a seal surface that surrounds the capillary tubes and forms a seal between the needle cap and the catheter adapter.

5. The catheter assembly of claim 4, wherein the needle cap comprises a tube that forms the seal surface.

6. The catheter assembly of claim 5, wherein the tube includes one or more pleats.

7. The catheter assembly of claim 6, wherein the one or more pleats comprise portions of the tube having a reduced thickness.

8. The catheter assembly of claim 1, wherein at least one of the capillary tubes includes an absorbent material.

9. The catheter assembly of claim 1, wherein the needle cap comprises one or more vents to facilitate the flow of air or fluids through the needle cap.

10. The catheter assembly of claim 9, wherein the one or more vents comprise a front vent and a rear vent.

11. The catheter assembly of claim 1, wherein the capillary tubes are uniformly spaced around the needle port.

12. A catheter assembly comprising:
a catheter adapter having a proximal end and a distal end;
a catheter that extends from the distal end of the catheter adapter; and
a needle assembly, the needle assembly comprising:
a needle hub configured to attach to the proximal end of the catheter adapter;
a needle having a proximal end secured within the needle hub and a distal end that extends out through the distal end of the catheter when the needle hub is attached to the catheter adapter; and
a needle cap having a needle port forming an opening through the needle cap through which the needle extends, the needle cap being configured to capture the distal end of the needle when the needle hub is detached from the proximal end of the catheter adapter, the needle cap including a plurality of capillary tubes that extend in parallel with at least a portion of the needle port, each capillary tube having a distal opening that is adjacent a distal opening of the needle port such that blood present at the distal opening of the needle port will be collected within one or more of the capillary tubes.

13. The catheter assembly of claim 12, wherein the needle assembly further comprises a tether that secures the needle cap to the needle hub when the needle hub is detached from the catheter adapter.

14. The catheter assembly of claim 12, wherein the needle cap comprises a seal surface that surrounds the capillary tubes and forms a seal between the needle cap and the catheter adapter.

15. The catheter assembly of claim 14, wherein the needle cap comprises a tube that forms the seal surface.

16. The catheter assembly of claim 15, wherein the tube includes one or more pleats.

17. The catheter assembly of claim 12, wherein at least one of the capillary tubes includes an absorbent material.

18. The catheter assembly of claim 12, wherein the needle cap comprises one or more vents to facilitate the flow of air or fluids through the needle cap.

19. The catheter assembly of claim 12, wherein the one or more vents comprise a front vent and a rear vent.

20. The catheter assembly of claim 12, wherein the capillary tubes are uniformly spaced around the needle port.

* * * * *